US012778741B2

(12) United States Patent
Singh et al.

(10) Patent No.: US 12,778,741 B2
(45) Date of Patent: Nov. 3, 2026

(54) 3D PRINTED BANDAGES

(71) Applicant: Saint Joseph's University, Philadelphia, PA (US)

(72) Inventors: Mahima Singh, Philadelphia, PA (US); Sriramakamal Jonnalagadda, Eagleville, PA (US)

(73) Assignee: Saint Joseph's University, Philadelphia, PA (US)

( * ) Notice: Subject to any disclaimer, the term of this patent is extended or adjusted under 35 U.S.C. 154(b) by 539 days.

(21) Appl. No.: 17/155,295

(22) Filed: Jan. 22, 2021

(65) Prior Publication Data

US 2021/0228332 A1 Jul. 29, 2021

Related U.S. Application Data

(60) Provisional application No. 62/964,757, filed on Jan. 23, 2020.

(51) Int. Cl.

| | |
|---|---|
| *A61F 2/10* | (2006.01) |
| *A61F 13/00* | (2024.01) |
| *A61K 31/7036* | (2006.01) |
| *A61K 38/18* | (2006.01) |
| *A61K 45/06* | (2006.01) |

(Continued)

(52) U.S. Cl.

CPC .......... *A61F 2/105* (2013.01); *A61K 31/7036* (2013.01); *A61K 38/1808* (2013.01); *A61K 45/06* (2013.01); *A61L 15/40* (2013.01); *A61L 15/44* (2013.01); *A61L 27/18* (2013.01); *A61L 27/34* (2013.01); *A61L 27/3813* (2013.01); *A61L 27/54* (2013.01); *A61L 27/60* (2013.01); *A61F 13/00063* (2013.01);

(Continued)

(58) Field of Classification Search

CPC ................ A61F 2/105; A61F 13/00063; A61F 2240/001; A61F 2250/0067; A61K 31/7036; A61K 38/1808; A61K 45/06; A61L 15/40; A61L 15/44; A61L 27/18; A61L 27/34; A61L 27/3813; A61L 27/60; A61L 2300/406; A61L 31/16; A61L 31/14; A61B 17/00

USPC ........................................... 606/213; 442/123

See application file for complete search history.

(56) References Cited

U.S. PATENT DOCUMENTS

2009/0004239 A1 * 1/2009 Ladet ...................... A61L 27/48 424/423
2014/0336700 A1 * 11/2014 Dave ....................... A61L 31/16 606/213

(Continued)

FOREIGN PATENT DOCUMENTS

JP 2002200176 * 1/2002

OTHER PUBLICATIONS

Polysciences, Poly(L-lactic acid), accessed online Apr. 26, 2024.*

(Continued)

*Primary Examiner* — Camie S Thompson

(74) *Attorney, Agent, or Firm* — Saul Ewing LLP; Domingos J. Silva; Kevin T. O'Brien

(57) ABSTRACT

The present invention provides a printed scaffold mat comprising a plurality of fused fibers comprising a first polymer; a coating comprising a second polymer, wherein the coating coats at least a portion of the surface of the plurality of fused fibers; and at least one pharmaceutical compound dispersed within the coating.

10 Claims, 11 Drawing Sheets

(51) Int. Cl.

| | |
|---|---|
| ***A61L 15/40*** | (2006.01) |
| ***A61L 15/44*** | (2006.01) |
| ***A61L 27/18*** | (2006.01) |
| ***A61L 27/34*** | (2006.01) |
| ***A61L 27/38*** | (2006.01) |
| ***A61L 27/54*** | (2006.01) |
| ***A61L 27/60*** | (2006.01) |

(52) U.S. Cl.
CPC ............... *A61F 2013/00157* (2013.01); *A61F 2240/001* (2013.01); *A61F 2250/0067* (2013.01); *A61L 2300/406* (2013.01)

(56) References Cited

U.S. PATENT DOCUMENTS

| | | | | |
|---|---|---|---|---|
| 2020/0253713 | A1* | 8/2020 | Rocco | A61L 27/18 |
| 2020/0276007 | A1* | 9/2020 | Musara | A61F 2/0063 |
| 2021/0161645 | A1* | 6/2021 | Rocco | D04C 1/06 |
| 2022/0134068 | A1* | 5/2022 | Zussman | A61K 47/34<br>604/891.1 |
| 2022/0403327 | A1* | 12/2022 | Ajji | B33Y 70/00 |

OTHER PUBLICATIONS

Polysciences, Polyethylene Glycol, accesed online Apr. 26, 2024.*

Polysciences, Polyethylene Glycol 400, accessed online Apr. 27, 2024.*

Gupta, et al., "Quantitation of Amikacin, Kanamycin, Neomycin, and Tobramycin in Pharmaceutical Dosage Forms Using the Hantzsch Reaction", Journal of Pharmaceutical Sciences, vol. 72, No. 12, Dec 1983, pp. 1470-1471.

Swaminathan, et al., "Physical characterization of thin semi-porous poly(L-lactic acid)/poly(ethylene glycol) membranes for tissue engineering", J Biomater Sci Polymer Edn, vol. 18, No. 10, 2007, pp. 1321-1333.

Singh, et al., Abstract, M1430-07-48—"Dermal Wound Bandages Made from 3D Printed Poly-1-Lactic Acid Mats Coated with Polyethylene Glybol and Loaded with Neomycin," Poster Presentation at American Association of Pharmaceutical Scientists (AAPS), available online to AAPS participants on Sep. 23, 2019, AAPS PharmSci 360 Meeting Nov. 3-6, 2019 in San Antonio, TX.

Singh, et al., "Dermal Wound Bandages Made from 3D Printed Poly-L-Lactic Acid Mats Coated with Polyethylene Glycol and Loaded with Neomycin," Poster Presentation at American Association of Pharmaceutical Scientists (AAPS) PharmSci 360, Nov. 4, 2019 in San Antonio, TX.

* cited by examiner

3D PRINTED BANDAGES

CROSS-REFERENCE TO RELATED APPLICATIONS

This application claims priority under 35 U.S.C. § 119(e) to U.S. Provisional Patent Application No. 62/964,757, filed Jan. 23, 2020, the contents of which are incorporated by reference herein in their entirety.

BACKGROUND OF THE INVENTION

In 2015, fire and heat resulted in 67 million injuries worldwide, causing about 2.9 million hospitalizations and 176,000 deaths overall. Most deaths due to burns occur in the developing world, particularly in Southeast Asia. The American Burn Association states that in the United States hospitalizations related to burn injury reach about 40,000 annually, including 30,000 at hospital burn centers (according to the 2010 National Hospital Discharge Survey).

Currently available bandage and wound covers, while substantially improved over those used previously, leave room for improvement. The current invention meets this need.

SUMMARY OF THE INVENTION

In certain embodiments, the present invention provides a printed scaffold mat having a plurality of fused fibers comprising a first polymer, a coating comprising a second polymer, wherein the coating coats at least a portion of the surface of the plurality of fused fibers; and at least one pharmaceutical compound dispersed within the coating.

In some embodiments, the first polymer includes at least one synthetic polymer comprising at least one copolymer of lactic acid monomers. In some embodiments, the at least one copolymer includes poly-L-lactic acid (PLLA), poly-lactide-co-glycolide (PLGA), or any combinations thereof. In some embodiments, the PLLA has a molecular weight of about 80 kDa to about 120 KDa. In some embodiments, the PLLA has a melting temperature of about 175° C. to about 180° C.

In some embodiments, the second polymer includes at least one synthetic hydrophilic polymer selected from the group consisting of polyethylene glycol (PEG), polyvinyl acetate (PVA), and any combinations thereof.

In some embodiments, the pharmaceutical compound includes at least one selected from the group consisting of antibiotics, growth factors, anti-inflammatory compounds, analgesic compounds, and any combinations thereof. In some embodiments, the antibiotic includes aminoglycoside and/or neomycin. In some embodiments, the growth factor is epidermal growth factor (EGF). In some embodiments, the growth factor includes at least one selected from the group consisting of keratocyte growth factor (KGF), fibroblast growth factor (FGF), vascular endothelial growth factor (VEGF), epidermal growth factor (EGF), and any combinations thereof.

In some embodiments, the second polymer includes polyethylene glycol having a molecular weight selected from 400 Da, 6 kDa, 20 kDa, and any combinations thereof.

In certain embodiments, the printed scaffold further includes a plurality of seeded cells. In some embodiments, the plurality of cells include at least one selected from the group consisting of keratinocytes, epidermal fibroblasts, keratinocyte progenitor cells, melanocytes, mesenchymal stem cells (MSCs), and any combinations thereof.

In certain aspects, the present invention provides a method of generating a skin graft including: printing a first synthetic polymer into a mat including a plurality of fibers; and, coating the mat at least partially with a second synthetic polymer.

In some embodiments, the second synthetic polymer is mixed with at least one pharmaceutical compound. In some embodiments, the at least one pharmaceutical compound includes at least one selected from the group consisting of antibiotics, growth factors, anti-inflammatory compounds, analgesic compounds, and any combinations thereof. In some embodiments, the antibiotics include neomycin and/or aminoglycoside.

In some embodiments, the first synthetic polymer includes PLLA.

In some embodiments, the second synthetic polymer includes PEG. In some embodiments, the PEG has a molecular weight of selected from the group consisting of: 400 Da, 6 kDa, and 20 kDa, and any combinations thereof.

In some embodiments, the method further includes seeding the coated mat with a plurality of cells. In some embodiments, the plurality of cells include one or more selected from the group consisting of: keratinocytes, epidermal fibroblasts, keratinocyte progenitor cells, melanocytes, mesenchymal stem cells (MSCs), and any combinations thereof.

DETAILED DESCRIPTION

Definitions

Figure 1:
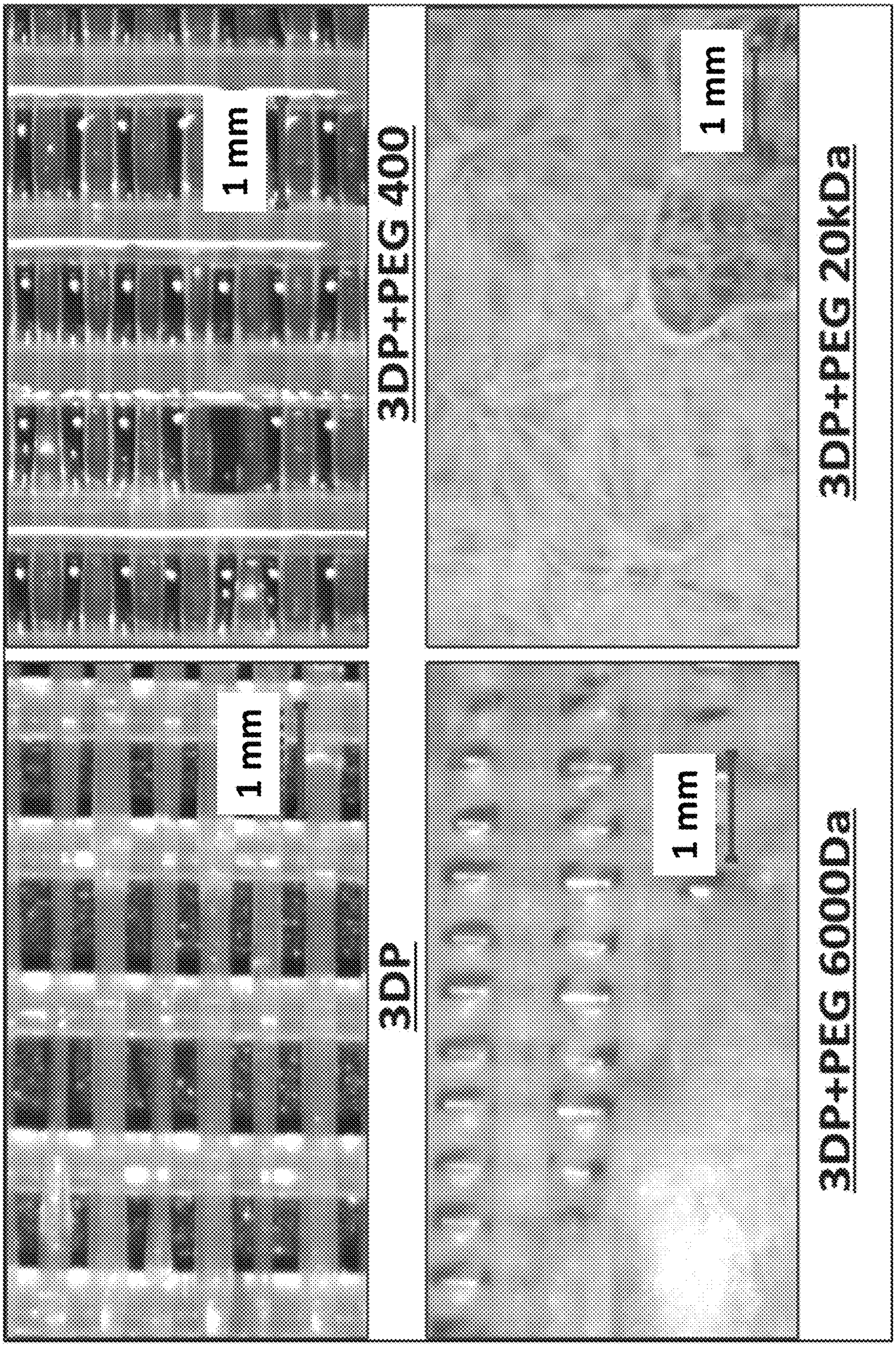
FIG. 1 depicts exemplary 3D printed mats, as contemplated herein, coated with polyethylene glycol (PEG).

Unless defined otherwise, all technical and scientific terms used herein have the same meaning as commonly understood by one of ordinary skill in the art to which this invention belongs. Although any methods and materials similar or equivalent to those described herein can be used in the practice or testing of the present invention, the preferred methods and materials are described.

As used herein, each of the following terms has the meaning associated with it in this section.

The articles "a" and "an" are used herein to refer to one or to more than one (i.e., to at least one) of the grammatical object of the article. By way of example, "an element" means one element or more than one element.

"About" as used herein when referring to a measurable value such as an amount, a temporal duration, and the like, is meant to encompass variations of ±20%, ±10%, ±5%, ±1%, or ±0.1% from the specified value, as such variations are appropriate to perform the disclosed methods.

Ranges: throughout this disclosure, various aspects of the invention can be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 2.7, 3, 4, 5, 5.3, and 6. This applies regardless of the breadth of the range.

Description

The present invention provides in one aspect compositions and methods for treating wounds in the subject. The compositions include printed scaffold mats prepared from 3D printed biocompatible polymers. The mats may be coated in one or more polymers, one or more pharmaceutical compounds, and/or any combinations thereof. The mats may be placed on a wound to help promote healing. The wound may be a burn wound. The wound may be one a subject including a human subject.

Compositions/Devices

The present invention provides printed scaffold mats for use as synthetic bandages for treating wounds in a subject. The synthetic mats of the present invention include a plurality of printed fibers. The mat may include a coating. The coating may be formed from a second polymer. The second polymer may include one or more pharmaceutical compounds.

The first polymer used to print the plurality of printed fibers may include any suitable polymer as understood in the art. For example, the first polymer may include one or more synthetic polymers such as one or more copolymers of lactic acid monomers [e.g., poly-L-lactic acid (PLLA), poly-lactide-co-glycolide (PLGAs)], and any combinations thereof. The PLLA may include PLLA having a molecular weight of up to about 80 kDa, about 80 kDa to about 100 kDa, about 100 kDa to about 120 kDa, including any and all molecular weights therebetween, and/or any combinations thereof. The PLLA may include PLLA having a melting point of between about 175° C. and about 180° C.

The plurality of printed fibers may be printed using any 3D printing technique as understood in the art, for example hot melt extrusion printing. The fibers may be printed using any technique or combinations of techniques including, for example fused deposition modeling, stereolithography, digital light processing, selective laser sintering, selective laser melting, laminated object manufacturing, digital beam melting, and the like. The printed fibers may have a diameter of about 0.5 mm. The diameter may include about 0.1 mm to about 0.2 mm, about 0.2 mm to about 0.3 mm, about 0.3 mm to about 0.4 mm, about 0.4 mm to about 0.5 mm, about 0.5 mm to about 0.6 mm, about 0.6 mm to about 0.7 mm, about 0.7 mm to about 0.8 mm, about 0.8 mm to about 0.9 mm, about 0.9 mm to about 1.0 mm. The diameter may include about 0.1 mm to about 0.5 mm, about 0.5 mm to about 1.0 mm, about 1 mm to about 1.5 mm, about 1.5 mm to about 2.0 mm, about 2.0 mm to about 2.5 mm, about 2.5 mm to about 3.0 mm, about 3.0 mm to about 3.5 mm, about 3.5 mm to about 4.0 mm, about 4.0 mm to about 4.5 mm, about 4.5 mm to about 5.0 mm, and the like.

The printed fibers may be printed into a mat pattern. The printed mat may have any suitable dimensions as understood by one skilled in the art. For example, the mat may have dimensions sufficiently suitable for dressing a particular wound width. The mat may be printed into any shape pattern as contemplated by one skilled in the art, non-limiting examples including square, rectangle, circle, oval, and the like. In some embodiments, the mat is printed into a square or rectangular pattern.

In some embodiments, the mat has a width of up to about 1 mm, about 1 mm to about 5 mm, about 5 mm to about 10 mm, about 10 mm to about 15 mm, about 15 mm to about 20 mm, about 20 mm to about 25 mm, about 25 mm to about 30 mm, about 30 mm to about 35 mm, about 35 mm to about 40 mm, about 40 mm to about 45 mm, about 45 mm to about 50 mm, about 50 mm to about 55 mm about 55 mm to about 60 mm, about 60 mm to about 65 mm, about 65 mm to about 70 mm, about 70 mm to about 75 mm, about 75 mm to about 80 mm, about 80 mm to about 85 mm, about 85 mm to about 90 mm, about 90 mm to about 95 mm, about 95 mm to about 100 mm, and the like.

In some embodiments, the mat has a length of up to about 1 mm, about 1 mm to about 5 mm, about 5 mm to about 10 mm, about 10 mm to about 15 mm, about 15 mm to about 20 mm, about 20 mm to about 25 mm, about 25 mm to about 30 mm, about 30 mm to about 35 mm, about 35 mm to about 40 mm, about 40 mm to about 45 mm, about 45 mm to about 50 mm, about 50 mm to about 55 mm, about 55 mm to about 60 mm, about 60 mm to about 65 mm, about 65 mm to about 70 mm, about 70 mm to about 75 mm, about 75 mm to about 80 mm, about 80 mm to about 85 mm, about 85 mm to about 90 mm, about 90 mm to about 95 mm, about 95 mm to about 100 mm, and the like.

The printed fibers may be fused together using any suitable technique as understood in the art. For example the fibers may be heat-fused, sintered, melted together, glued, epoxied, and the like.

The mat may include a coating formed from a second synthetic polymer. The coating may include any suitable biocompatible synthetic hydrophilic polymer as understood in the art. For example, the polymer coating may include one or more of polyethylene glycol (PEG), polyvinyl acetate (PVA), and the like, and any combinations thereof. The PEG may include PEG having a molecular weight of up to 400 Da, about 400 Da, about 400 Da to about 1 kDa, about 1 kDa to about 6 kD, about 6 kDa, about 6 kDa to about 10 kDa, about 10 kDa to about 20 kDa, about 20 kDa, including all molecular weights therebetween, and/or any combinations thereof. The coating polymer may coat at least a portion of the surface of the plurality of fused fibers. In some embodiments, the coating may entirely coat the plurality of fused fibers forming a mat.

The coating may include one or more pharmaceutical compounds. The pharmaceutical compounds may be mixed or dispersed within the coating, coated on top of the coating, and/or any combinations thereof. The pharmaceutical compounds may include one or more of antibiotics, growth factors, anti-inflammatory compounds, analgesic compounds, and any combinations thereof. The antibiotics may include one or more of aminoglycoside, neomycin, and/or any combinations thereof. The growth factors may include one or more of epidermal growth factor (EGF), keratocyte growth factor (KGF), fibroblast growth factor (FGF), vascular endothelial growth factor (VEGF), and any combinations thereof.

The printed scaffold may be seeded with a plurality of cells. The plurality of cells may include any suitable cell as understood in the art for improving a wound. For example, the plurality of cells may include one or more of keratinocytes, epidermal fibroblasts, keratinocyte progenitor cells, melanocytes, mesenchymal stem cells (MSCs), and/or any combinations thereof.

Methods

The present invention provides in one aspect methods for preparing and generating skin grafts and methods for treating a wound or improving a wound in a subject.

Figure 10:
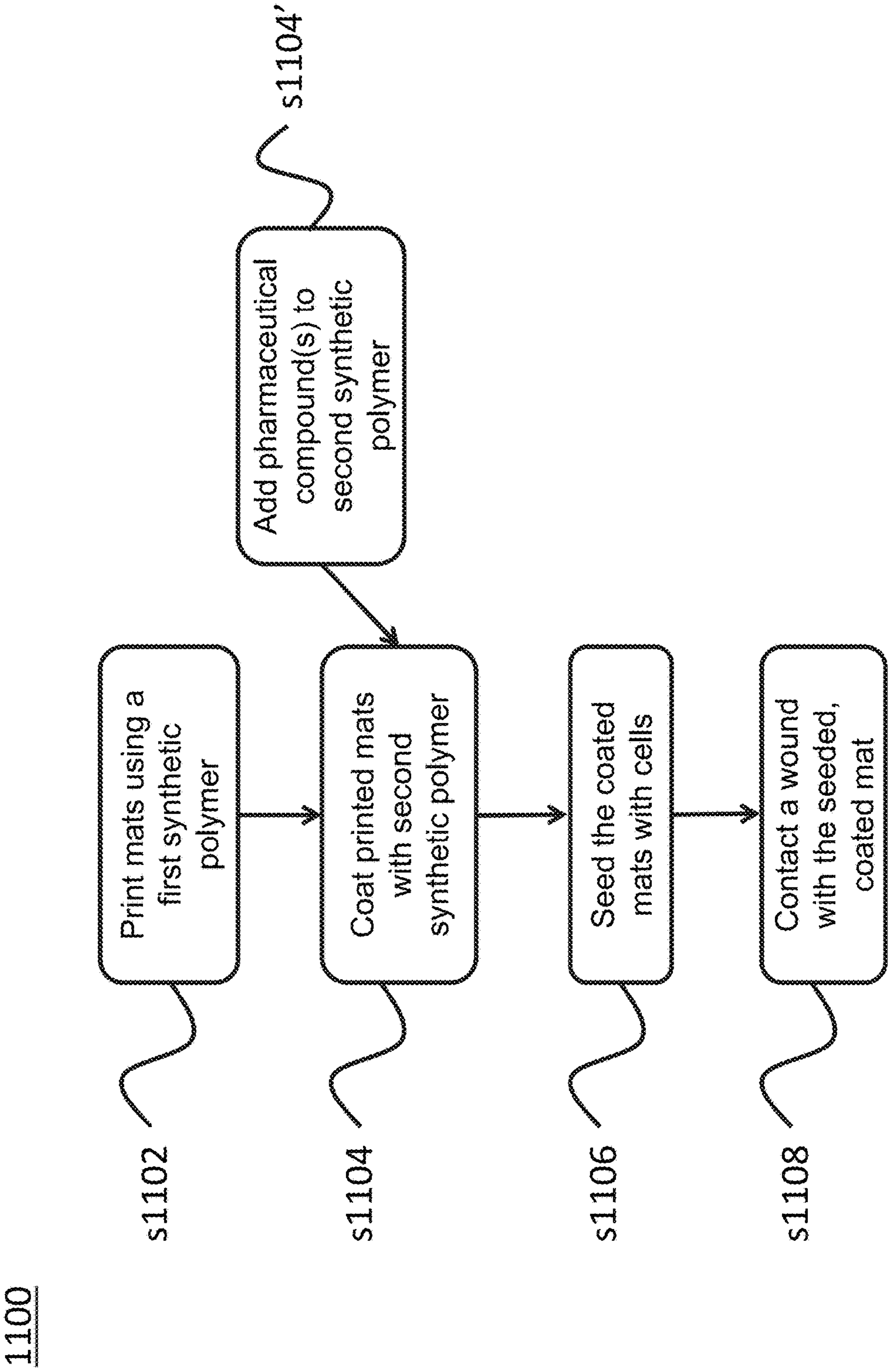
FIG. 10 depicts an exemplary method of the present invention.

Referring now to FIG. 10, the present invention provides method 1100 for preparing one or more mats as contemplated herein. Embodiments of step 1102 of method 1100 may include first printing a plurality of fibers using any suitable technique as understood in the art. The plurality of fibers may be printed using one or more 3D printing techniques including for example, hot melt-extrusion printing. In some embodiments, the plurality of fibers are printed using one or more of fused deposition modeling, stereolithography, digital light processing, selective laser sintering, selective laser melting, laminated object manufacturing, digital beam melting, and/or any combinations thereof. The plurality of fibers are printed in a mesh.

The mats may be printed using any suitable material as understood in the art. For example, the mats may be formed by printing one or more of a first synthetic polymer into fibers. The first synthetic polymer may include one or more biocompatible synthetic polymers such as one or more copolymers of lactic acid monomers. For example, the first synthetic polymer may include poly-L-lactic acid (PLLA), poly-lactide-co-glycolide (PLGAs), and/or any combinations thereof, as described herein. The hot-melt extruded fibers are formed into mats. The printed fibers have a diameter of about 0.5 mm. The diameter of the printed fibers may be about 0.1 mm to about 0.2 mm, about 0.2 mm to about 0.3 mm, about 0.3 mm to about 0.4 mm, about 0.4 mm to about 0.5 mm, about 0.5 mm to about 0.6 mm, about 0.6 mm to about 0.7 mm, about 0.7 mm to about 0.8 mm, about 0.8 mm to about 0.9 mm, about 0.9 mm to about 1 mm, and so on. The printed fibers are printed into the form of one or more mats. The mats may be printed into any suitable cross-sectional shape as understood in the art, including, for example, a square, rectangle, circle, oval, trapezoid, triangle, and the like. In some embodiments, the mats are printed into a square or rectangular shape have a length and width of about 40 mm. In some embodiments, the mats have a length of about 1 mm to about 5 mm, about 5 mm to about 10 mm, about 10 mm to about 20 mm, about 20 mm to about 30 mm, about 30 mm to about 40 mm, about 40 mm to about 50 mm, about 50 mm to about 60 mm, about 60 mm to about 70 mm, about 70 mm to about 80 mm, about 80 mm to about 90 mm, about 90 mm to about 100 mm, or greater than about 100 mm. In some embodiments, the mats have a width of about 1 mm to about 5 mm, about 5 mm to about 10 mm about 10 mm to about 20 mm, about 20 mm to about 30 mm, about 30 mm to about 40 mm, about 40 mm to about 50 mm, about 50 mm to about 60 mm, about 60 mm to about 70 mm, about 70 mm to about 80 mm, about 80 mm to about 90 mm, about 90 mm to about 100 mm or greater than about 100 mm.

Embodiments of step s1104 include coating the mat with a second synthetic polymer. The second synthetic polymer may include any suitable biocompatible synthetic hydrophilic polymer as described herein. For example, the polymer coating may include one or more of polyethylene glycol (PEG), polyvinyl acetate (PVA), and/or any combinations thereof. The PEG may include PEG having a molecular weight of up to 400 Da, about 400 Da, about 400 Da to about 1 kDa, about 1 kDa to about 6 kD, about 6 kDa, about 6 kDa to about 10 kDa, about 10 kDa to about 20 kDa, about 20 kDa, including all molecular weights therebetween, and/or any combinations thereof. The second synthetic polymer may be prepared into a molten form. The one or mats prepared in step s1102 may be coated with the second synthetic polymer using one or more suitable techniques including, for example, dipping, submerging, spraying, painting, and the like. The one or more mats may be at least partially coated with the second synthetic polymer. In some embodiments, the one or more mats are completely coated with the second synthetic polymer.

In some embodiments, method 1100 includes step s1104'. Embodiments of step s1104' include adding one or more pharmaceutical compounds to the second synthetic polymer. The one or more pharmaceutical compounds may be mixed into molten second synthetic polymer, dissolve within, dispersed within, coated on top of, or otherwise combined with the second synthetic compound. The pharmaceutical compound may include one or more of antibiotics, growth factors, anti-inflammatory compounds, analgesic compounds, and any combinations thereof. The antibiotics may include one or more of aminoglycoside, neomycin, and/or any combinations thereof. The growth factors may include one or more of epidermal growth factor (EGF), keratocyte growth factor (KGF), fibroblast growth factor (FGF), vascular endothelial growth factor (VEGF), and/or any combinations thereof.

In some embodiments, method 1100 may include step s1106. Embodiments of step s1106 include seeding one or more cells or populations of cells onto the one or more coated and printed mats as described herein. The one or more cells or populations of cells may include a plurality of one cell type and/or a mix of one or more cell types. The plurality of cells may include any suitable cell as understood in the art for improving a wound. For example, the plurality of cells may include one or more of keratinocytes, epidermal fibroblasts, keratinocyte progenitor cells, melanocytes, mesenchymal stem cells (MSCs), and/or any combinations thereof. The plurality of cells may be seeded onto the coated, printed mat using one or more suitable techniques as understood in the art.

Embodiments of step s1108 may include contacting the seeded, coated, printed mat with a wound in a subject. The wound may include one or more of a skin wound such as a burn, rash, cut, laceration, gash, scrape, abrasion, puncture, avulsion, and/or any combinations thereof. The one or more mats of the present invention may contact the wound for a duration including up to an hour, and hour to 24 hours, 24 hours to 5 days, 5 days to 7 days, 7 days to 14 days, or longer than 14 days. The mat may be placed on the wound and not removed, may resorb into the wound, and/or may be removed or be at least partially removed from the wound after a duration deemed suitable by one skilled in the art. The subject may include a mammalian subject, for example a human. In some embodiments, the subject includes a canine, equine, feline, murine, primate, bovine, porcine, and the like.

EXPERIMENTAL EXAMPLES

The invention is further described in detail by reference to the following experimental examples. These examples are provided for purposes of illustration only, and are not intended to be limiting unless otherwise specified. Thus, the invention should in no way be construed as being limited to the following examples, but rather, should be construed to encompass any and all variations which become evident as a result of the teaching provided herein.

Three dimensional (3D) printing via hot melt extrusion has been studied for fabrication of films and implants. Different molecular weight polyethylene glycols (PEG) were used to coat 3D printed poly-l-lactic acid (PLLA) mats to study the plasticization effects of PEG on the mats. The mats were then loaded with an antibiotic (neomycin) to study the feasibility of loading and release of the drug from the mats. The overall application of the mats for utilization as a dermal wound product depends on optimization of mechanical strength, porosity and drug release.

Materials and Methods

Creating Mats

Mats were printed using ZMorph 3D printer using 40% infill and dimensions 40 mm×40 mm×0.4 mm. PEG of MW 400 Da, 6 kDa, and 20 kDa were weighed and heated up to 60-70° C. on a glass petri dish and melted for 30 mins. 1 ml of 2.5% neomycin in solution was added to samples. All mats were soaked in PEG and neomycin for 24 hours and then washed using 70% ethanol. Images were taken for all mats using an AmScope microscope.

DSC Study

For DSC studies, a DSC822e (Mettler Toledo) was used to analyze samples using the STARe software. Samples were held at 25° C. isotherm for 5 minutes then heated at 10° C./min from 25° C.-200° C., 200° C.-25° C., 25° C.-200° C. and finally 200-25° C.

Mechanical Testing

For mechanical testing, a Shimadzu Autograph tensile tester with 50N load cell was used. Trapezium software was used to analyze all data. Individual fibers of dimensions 10 mm×0.5 mm were used for analysis. Maximum force at break (stress) and length of elastic elongation (strain) were recorded. Young's modulus was calculated using the slope of stress vs strain graphs.

Drug Release Study

A Hantzsch reaction was used to study neomycin release from the 3D printed and PEG coated mats. A Hantzsch solution was prepared at a pH of 2.5 using 0.6 M acetic acid, acetylacetone, 40% formaldehyde and water. Using a 1:1 mixture of Hantzsch and neomycin solution, a standard curve was prepared using absorbance measurements at 356 nm on a UV spectrophotometer. Drug release samples were drawn at 0.5 hr, 1 hr, 2 hr, 4 hr, 18 hr, 24 hr then daily up to 7 days then weekly up to 21 days.

Selected Results

Figure 2:
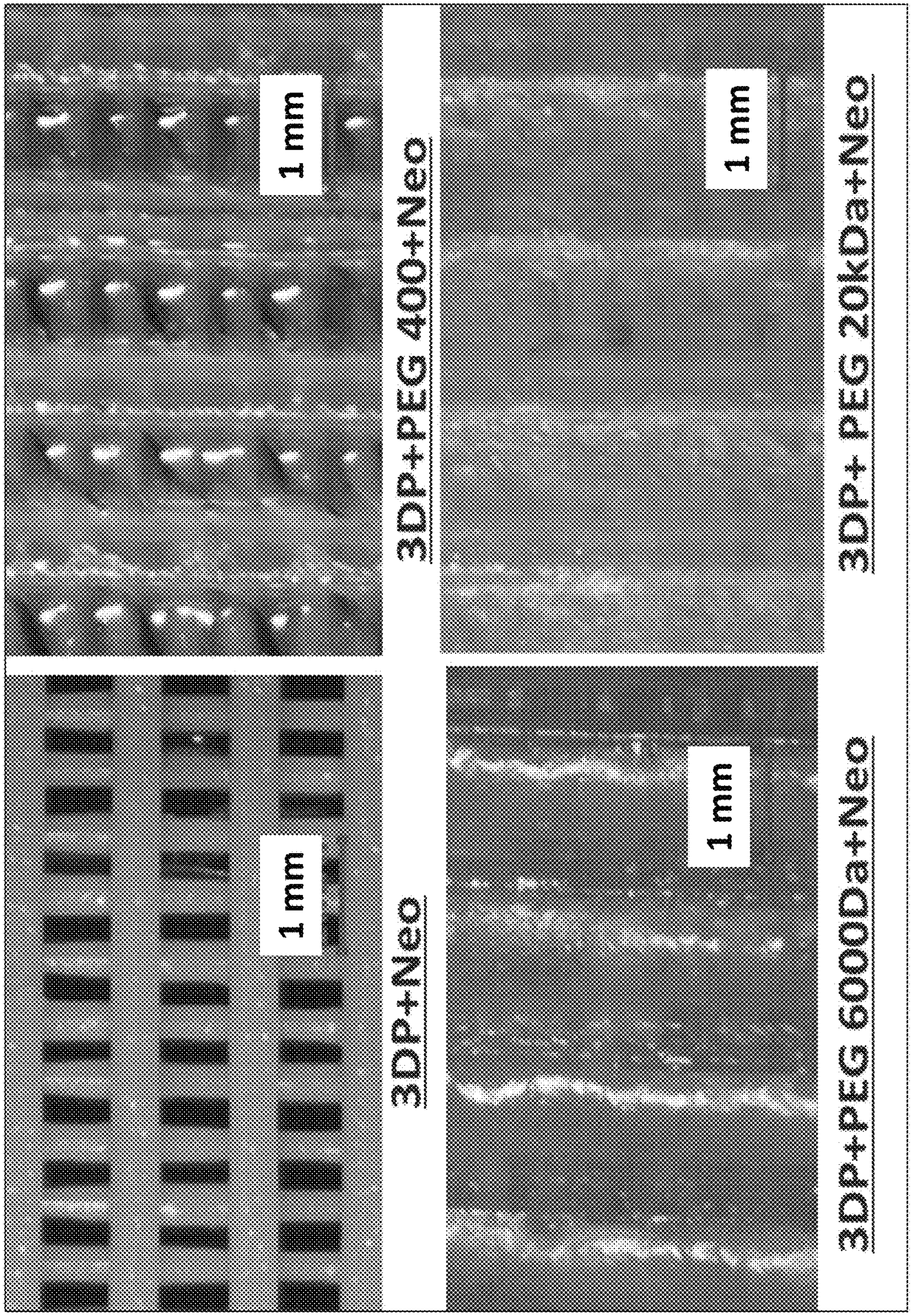
FIG. 2 depicts exemplary 3D printed mats coated with PEG and loaded with neomycin.

As shown in FIGS. 1 and 2, mats coated with PEG 400 had the most uniform coating.

Mats coated with PEG 6 kDa and 20 kDa had sludgy appearances. Neomycin distribution was consistent when dissolved with PEG 400 compared to other PEGs.

Figure 3:
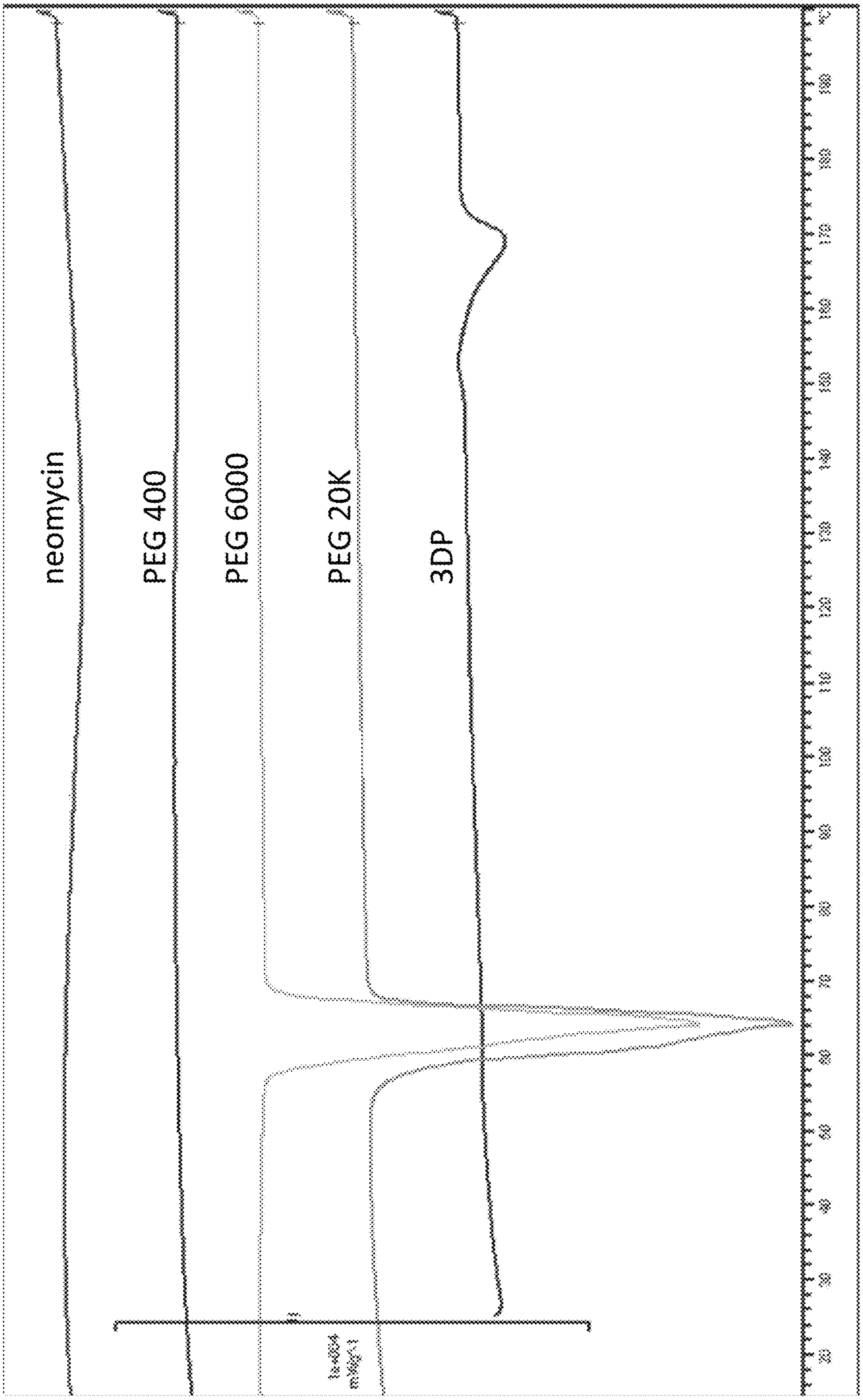
FIG. 3 depicts an exemplary DSC thermogram comparing certain mat materials.
Figure 4:
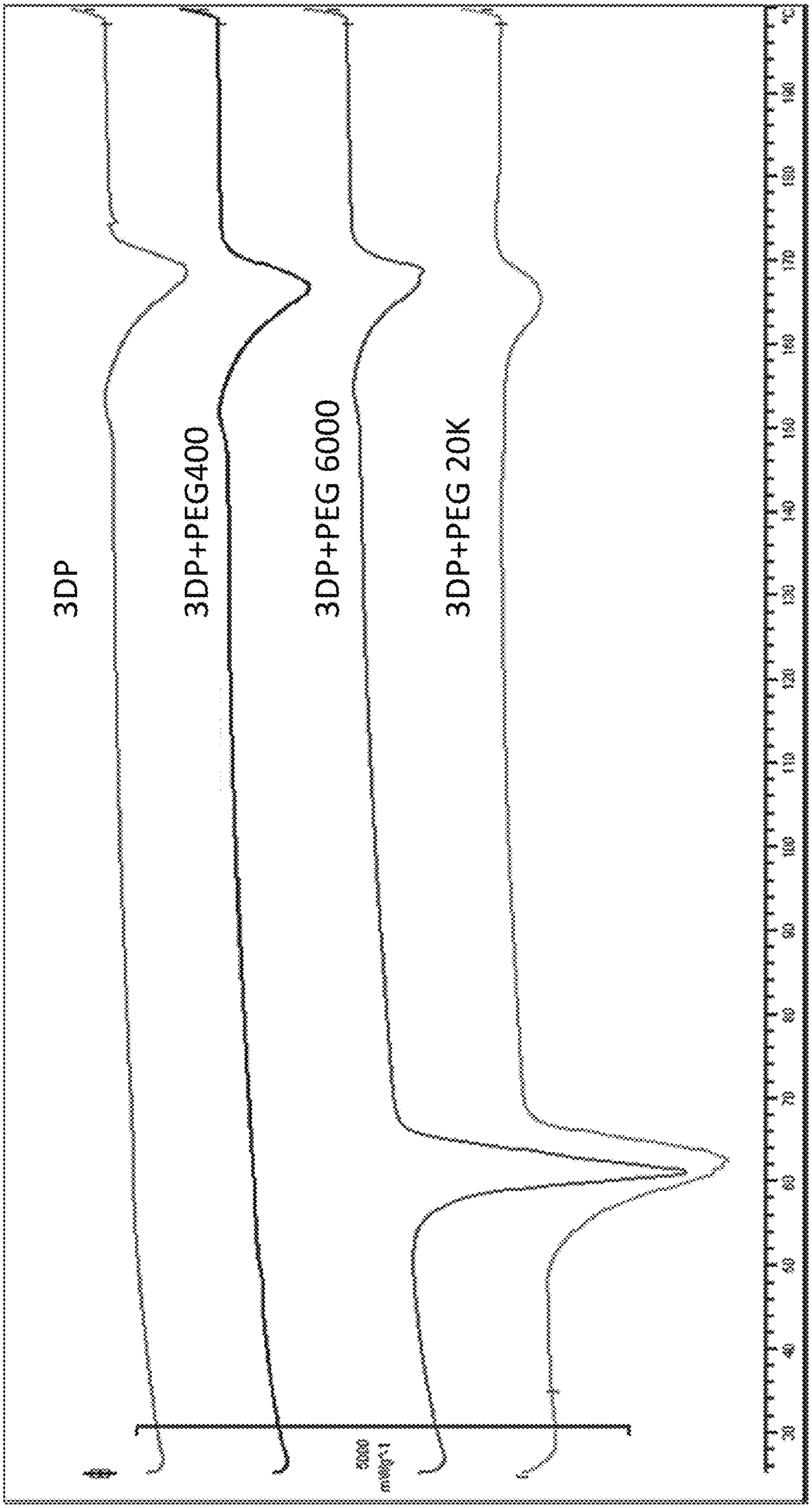
FIG. 4 depicts an exemplary DSC thermogram comparing certain mat samples coated with PEG.
Figure 6:
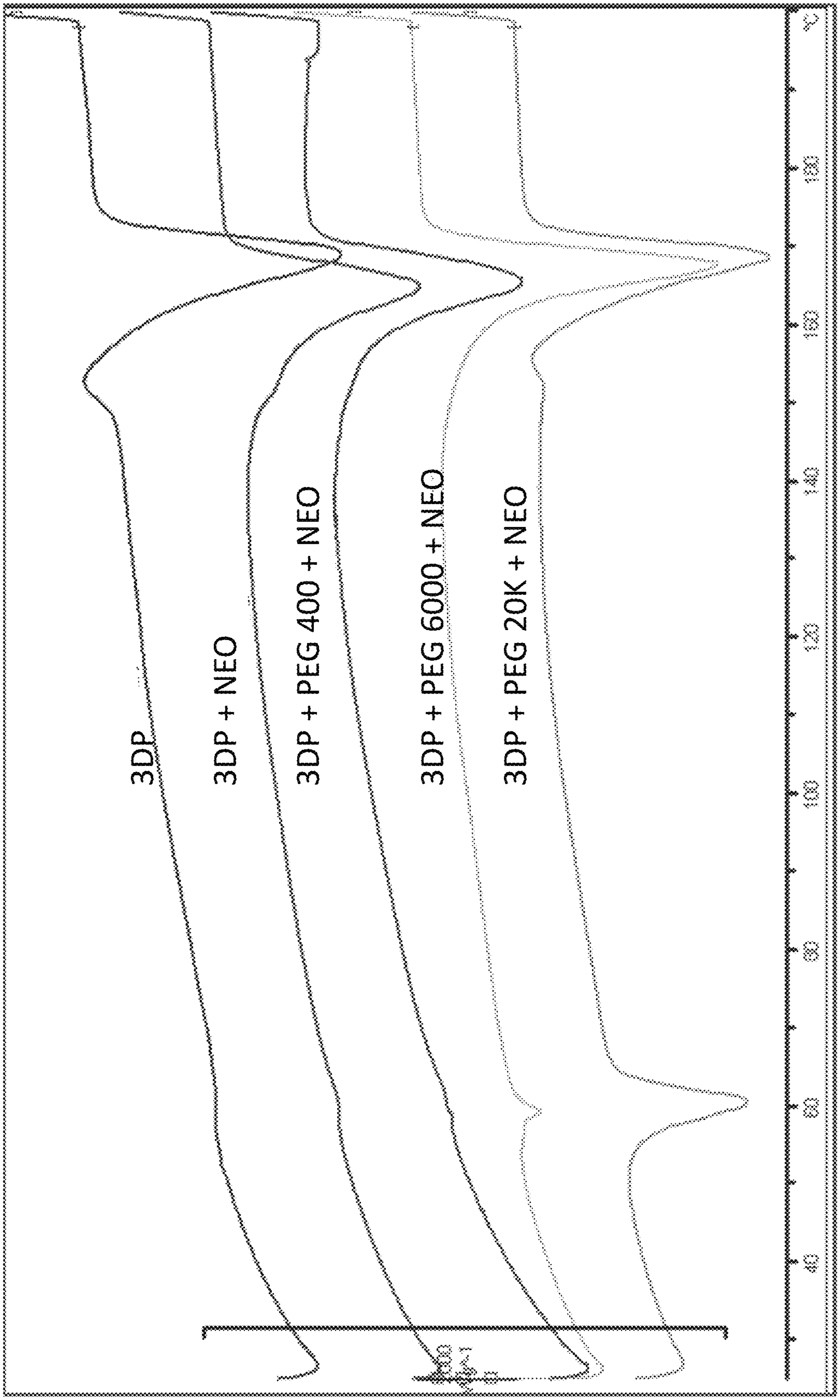
FIG. 6 depicts an exemplary DSC thermogram comparing certain mat samples coated with neomycin.

Thermograms from DSC studies, shown in FIGS. 3, 4 and 6, show miscibility of mats with PEG and neomycin. Heat of enthalpy (H) of 3D printed mats (44 J/g) decreased with addition of PEG 400 (34 J/g), PEG 6 kDa (26 J/g) and PEG 20 kDa (17 J/g). Addition of neomycin to the printed mats slightly increased the enthalpy of all mats: 3D printed+neomycin (45 J/g), 3D printed+PEG 400+neomycin (30 J/g), 3D printed+PEG 6 kDa+neomycin (34 J/g) and 3D printed+PEG 20 kDa+neomycin (35 J/g). These results are depict in FIG. 6.

Figure 5:
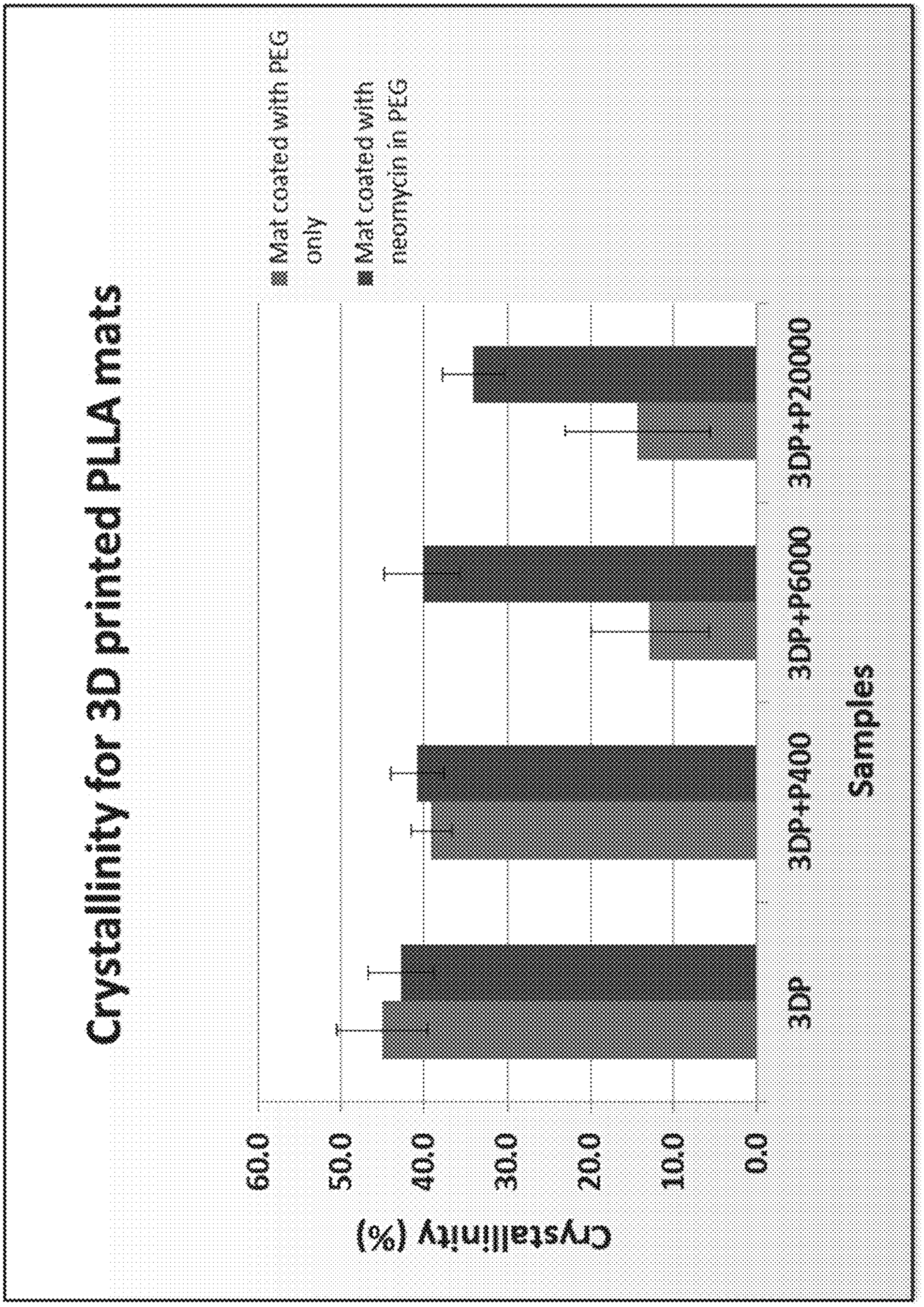
FIG. 5 depicts data comparing percentage crystallinity of mat samples coated with PEG and loaded with neomycin.

The degree of crystallinity of PLLA mats decreases with increase in MW of PEG, shown in FIG. 5: 3D mats-45.1%, 3D+PEG 400-39.1% (±2.4), 3D+PEG 6 kDa-12.8% (±7.1), and 3D+PEG 20 kDa-14.3% (±8.7). Further addition of neomycin decreases crystallinity as well but it is increased compared to coating with PEG alone: 3D+neomycin-42.7% (±4.0), 3D+PEG 400+neomycin-40.8% (±3.2), 3D+PEG 6 kDa+neomycin-40.2% (±4.6), and 3D+PEG 20 kDa+neomycin-34.1% (±3.8).

Figure 7:
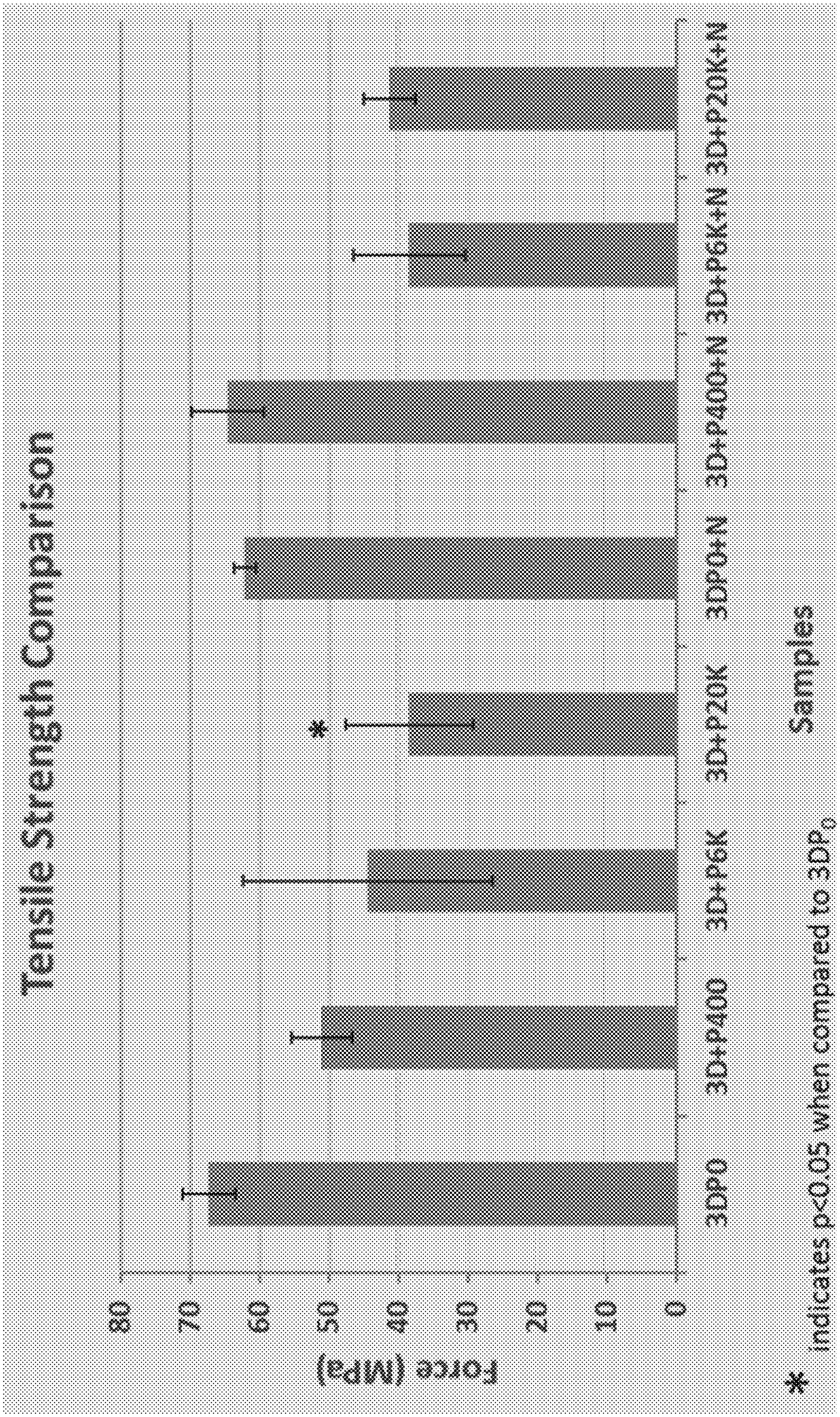
FIG. 7 depicts data comparing tensile strength of mat samples.
Figure 8:
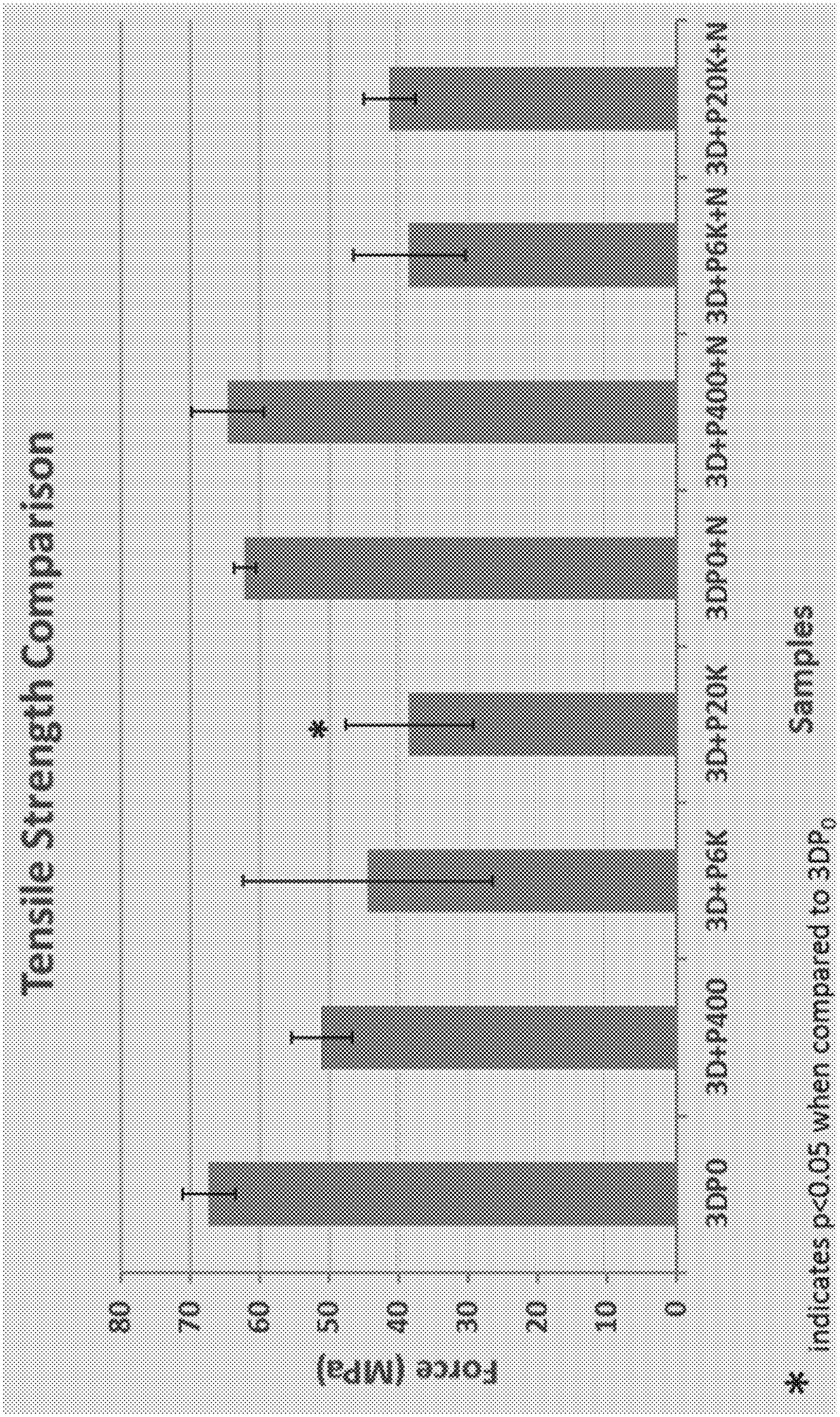
FIG. 8 depicts data comparing Young's modulus of mat samples.
Figure 9A:
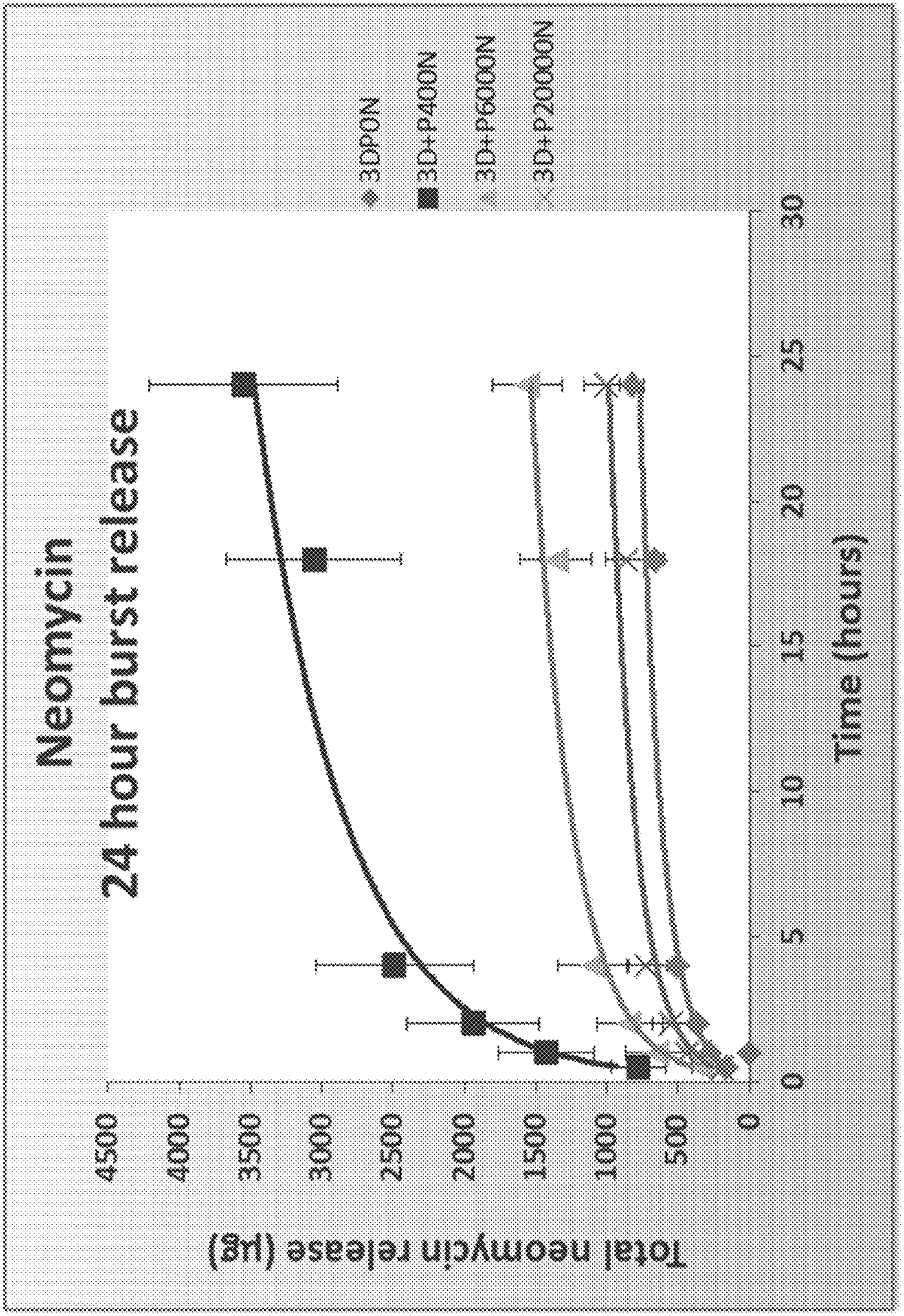
FIGS. 9A and 9B depict exemplary drug release profiles of neomycin over a twenty-four hour period.
Figure 9B:
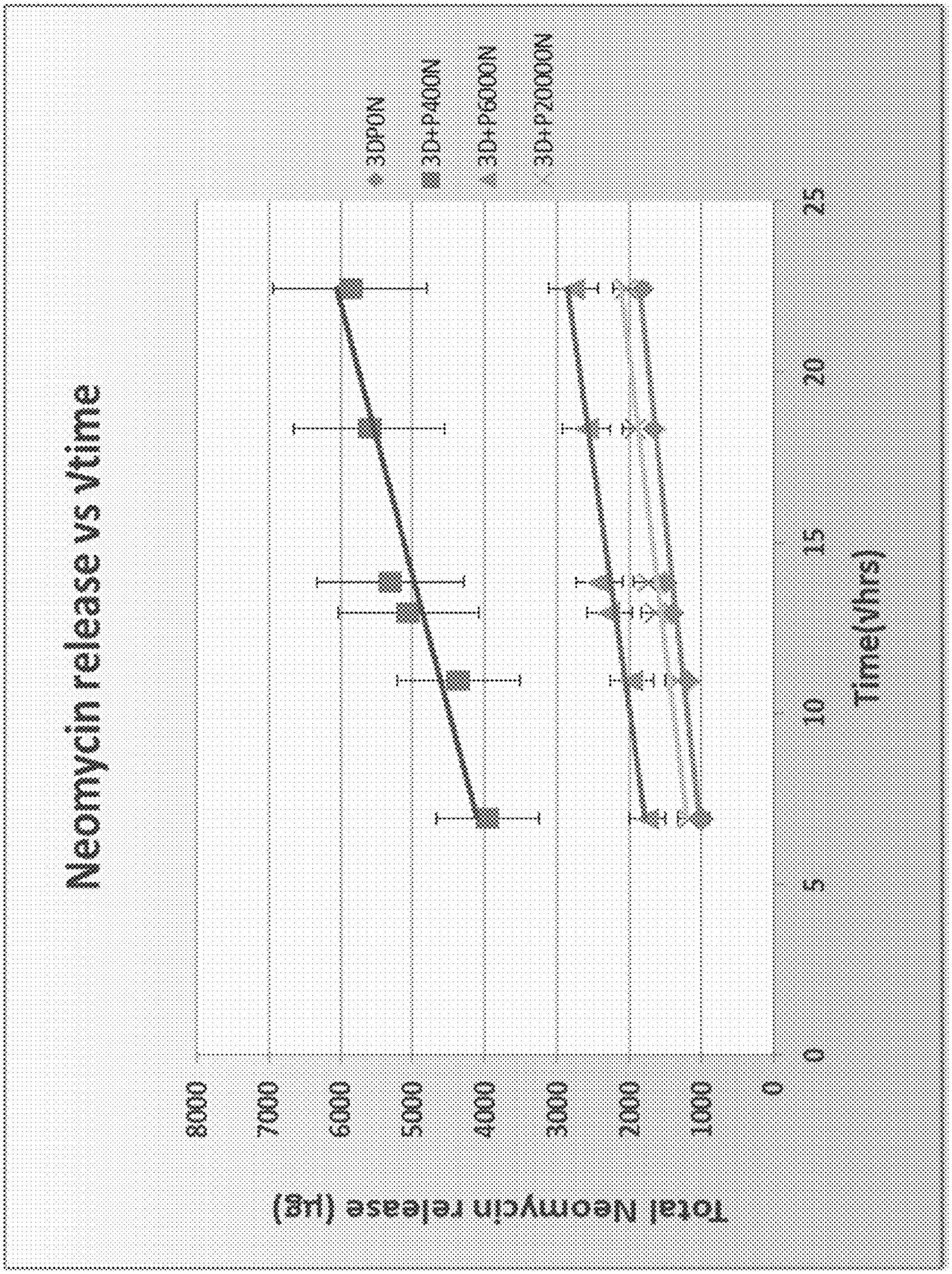

Tensile strength of 3D printed mats, shown in FIGS. 7 and 8, decreased with addition of PEG 400 from 67±3.8 MPa to 51.1±4.4 MPa. When loaded with neomycin, the tensile strength of 3DP+neomycin−62.2±1.5 MPa increases with addition of PEG 400−54.7±5.2 but decreases with PEG 6 kDa and 20 kDa respectively −38.5±8.1 and 41.3±3.8 MPa. 3D mats with PEG 400 had the lowest young's modulus at 32.4±1 MPa when compared to 3D mats alone 49±6.1 MPa. 3D mats coated with PEG 400 showed burst release up to 24 hours, shown in FIGS. 9A and 9B.

Mats were successfully printed using additive manufacturing. Mats were then coated with PEG to improve physical characteristics when compared to PLLA alone and loaded with neomycin to serve as dermal wound bandages. The soaking method of creating the mats was successful in incorporating PEG with PLLA especially PEG of MW 400. The incorporation of PEG in PLLA improves the flexibility of the mats and decreases the crystallinity of the PLLA mats allowing them to be suitable for further in vitro cell studies. This study allows 3D printed PLLA mats coated with PEG and loaded with neomycin to be a viable candidate for study in dermal wound applications.

OTHER EMBODIMENTS

The recitation of a listing of elements in any definition of a variable herein includes definitions of that variable as any single element or combination (or subcombination) of listed elements. The recitation of an embodiment herein includes that embodiment as any single embodiment or in combination with any other embodiments or portions thereof.

The disclosures of each and every patent, patent application, and publication cited herein are hereby incorporated herein by reference in their entirety. While this invention has been disclosed with reference to specific embodiments, it is apparent that other embodiments and variations of this invention may be devised by others skilled in the art without departing from the true spirit and scope of the invention. The appended claims are intended to be construed to include all such embodiments and equivalent variations.

The invention claimed is:

1. A printed scaffold mat comprising:

a 3D printed mesh mat of fused poly-L-lactic acid (PLLA) fibers; and a coating covering at least a portion of a surface of the 3D printed mesh mat, wherein the coating comprises polyethylene glycol (PEG) and neomycin dispersed within the PEG, wherein the PEG coated on PLLA fibers improves the flexibility and decreases the crystallinity of the 3D printed mesh mat as compared to a corresponding uncoated 3D printed mesh mat, wherein the mat is planar, and wherein the PEG has a molecular weight of up to 1 kDa.

2. The printed scaffold mat of claim 1, wherein the polyethylene glycol has a molecular weight of 400 Da.

3. The printed scaffold mat of claim 1, wherein the PLLA has a molecular weight of about 80 kDa to about 120 kDa.

4. The printed scaffold mat of claim 1, wherein the PLLA has a melting temperature of about 175° C. to about 180° C.

5. The printed scaffold of claim 1, further comprising a plurality of seeded cells.

6. The printed scaffold of claim 5, wherein the plurality of cells comprises at least one selected from the group consisting of keratinocyte, epidermal fibroblast, keratinocyte progenitor cell, melanocyte, mesenchymal stem cells (MSC), and any combinations thereof.

7. A method of generating a skin graft comprising:

3D printing a planar mesh mat of fused poly-L-lactic acid (PLLA) fibers;

mixing polyethylene glycol (PEG) and neomycin to prepare a coating mixture; and coating at least a portion of a surface of the 3D printed mesh mat with the coating mixture, wherein the PEG coated on PLLA fibers improves the flexibility and decreases the crystallinity of the 3D printed mesh mat as compared to a corresponding uncoated 3D printed mesh mat, and wherein the PEG has a molecular weight of up to 1 kDa.

8. The method of claim 7, wherein the PEG has a molecular weight of 400 Da.

9. The method of claim 7, further comprising seeding the coated mat with a plurality of cells.

10. The method of claim 9, wherein the plurality of cells comprises one or more selected from the group consisting of keratinocyte, epidermal fibroblast, keratinocyte progenitor cell, melanocyte, mesenchymal stem cell (MSC), and any combinations thereof.

* * * * *